United States Patent
Bladt et al.

(10) Patent No.: US 10,532,052 B2
(45) Date of Patent: *Jan. 14, 2020

(54) COMBINATION OF A 6-OXO-1,6-DIHYDRO-PYRIDAZINE DERIVATIVE HAVING ANTI-CANCER ACTIVITY WITH AN EGFR INHIBITOR

(71) Applicant: Merck Patent GmbH, Darmstadt (DE)

(72) Inventors: Friedhelm Bladt, Heidelberg (DE); Manja Friese-Hamim, Moerfelden-Walldorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,527

(22) PCT Filed: Nov. 12, 2015

(86) PCT No.: PCT/EP2015/002265
§ 371 (c)(1),
(2) Date: Jun. 9, 2017

(87) PCT Pub. No.: WO2016/091346
PCT Pub. Date: Jun. 16, 2016

(65) Prior Publication Data
US 2017/0319581 A1 Nov. 9, 2017

(30) Foreign Application Priority Data
Dec. 12, 2014 (EP) .................................... 14004200

(51) Int. Cl.
*A61K 31/506* (2006.01)
(52) U.S. Cl.
CPC .................. *A61K 31/506* (2013.01)
(58) Field of Classification Search
CPC . A61K 2300/00; A61K 31/506; A61K 31/517
See application file for complete search history.

(56) References Cited

U.S. PATENT DOCUMENTS

| | | | | |
|---|---|---|---|---|
| 8,329,692 | B2 * | 12/2012 | Schadt | C07D 401/10 514/236.5 |
| 8,580,781 | B2 | 11/2013 | Dorsch et al. | |
| 8,658,643 | B2 | 2/2014 | Schadt et al. | |
| 8,921,357 | B2 | 12/2014 | Dorsch et al. | |
| 8,927,540 | B2 | 1/2015 | Dorsch et al. | |
| 8,975,249 | B2 | 3/2015 | Lee et al. | |
| 9,056,839 | B2 | 6/2015 | Lai | |
| 9,062,029 | B2 * | 6/2015 | Schadt | C07D 401/10 |
| 9,284,300 | B2 | 3/2016 | Dorsch et al. | |
| 9,308,205 | B2 | 4/2016 | Becker et al. | |
| 9,340,524 | B2 | 5/2016 | Chen et al. | |
| 9,375,431 | B2 | 6/2016 | Lee et al. | |
| 9,403,799 | B2 | 8/2016 | Schadt et al. | |
| 9,539,255 | B2 | 1/2017 | Lai | |
| 9,867,824 | B2 | 1/2018 | Lee et al. | |
| 2010/0197690 | A1 | 8/2010 | Schadt et al. | |
| 2010/0234354 | A1 | 9/2010 | Dorsch et al. | |
| 2012/0149687 | A1 | 6/2012 | Lee et al. | |
| 2012/0189573 | A1 | 7/2012 | Ashkenazi | |
| 2012/0295908 | A1 | 11/2012 | Schadt et al. | |
| 2013/0184260 | A1 | 7/2013 | Dorsch et al. | |
| 2013/0184261 | A1 | 7/2013 | Dorsch et al. | |
| 2013/0267530 | A1 | 10/2013 | Lai | |
| 2014/0128396 | A1 | 5/2014 | Schadt et al. | |
| 2014/0199236 | A1 | 7/2014 | Chen et al. | |
| 2015/0011534 | A1 | 1/2015 | Dorsch et al. | |
| 2015/0044211 | A1 | 2/2015 | Bladt et al. | |
| 2015/0133452 | A1 | 5/2015 | Schadt et al. | |
| 2015/0246040 | A1 | 9/2015 | Lee et al. | |
| 2015/0297594 | A1 | 10/2015 | Bladt et al. | |
| 2016/0022677 | A1 | 1/2016 | Lai | |
| 2016/0220548 | A1 | 8/2016 | Chen et al. | |
| 2017/0027937 | A1 | 2/2017 | Lee et al. | |

FOREIGN PATENT DOCUMENTS

| | | |
|---|---|---|
| EA | 201101039 A1 | 2/2012 |
| JP | 2010532774 A | 10/2010 |
| JP | 2013541561 A | 11/2013 |
| RU | 2007134568 A | 3/2009 |
| WO | 2009/006959 A1 | 1/2009 |
| WO | 2009/007074 A1 | 1/2009 |
| WO | 2012/061299 A1 | 5/2012 |
| WO | 2013/138495 A1 | 9/2013 |
| WO | 13139423 A1 | 9/2013 |
| WO | 14056566 A1 | 4/2014 |
| WO | 2014056566 A1 | 4/2014 |
| WO | 2014/113260 A1 | 7/2014 |

OTHER PUBLICATIONS

International Search Report dated Jan. 4, 2016 issued in corresponding PCT/EP2015/002265 application (6 pages).
Written Opinion of the International Searching Authority dated Jan. 4, 2016 issued in corresponding PCT/EP2015/002265 application (5 pages).
Tjulandin S et al: Epidermal Growth Factor Receptor Tyrosine Kinase Inhibitors in Patients with Non-small Cell Lung Cancer: Ten Years Later. Malign Tumors 2012; T.1, 6-14.
Office Action in corresponding RU 2017124612 dated Jun. 5, 2019 (pp. 1-2).
Office Action in corresponding JP Application No. 2017-531477 dispatched Jul. 31, 2019 (pp. 1-2).
Ortiz-Cuaran et al: Attacking EGFR mutant lung cancer by combined EGFR and c-Met inhibition, Cancer Research, 2014, 74 (19) Suppl. 1, Abstract No. 1690.

(Continued)

*Primary Examiner* — Sabiha N Qazi
(74) *Attorney, Agent, or Firm* — Millen White Zelano and Branigan, PC; Csaba Henter

(57) ABSTRACT

A pharmaceutical composition of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof in combination with N-[3-[[2-[4-(4-acetylpiperazin-1-yl)-2-methoxy-anilino]-5-(trifluoromethyl)pyrimidin-4-yl]amino]phenyl]prop-2-enamide.

10 Claims, 2 Drawing Sheets

(56) References Cited

OTHER PUBLICATIONS

Bladt et al: The c-Met inhibitors EMD 1214063 and EMD 1204831 are effective in combination with EGFR and VEGF inhibitors in NSCLC models, Cancer Research, 2012, 72 Suppl. 8, Abstract No. 1787.
Bladt et al: EMD 1214063 and EMD 1204831 Constitute a New Class of Potent and Highly Selective c-Met Inhibitors, Clinical Cancer Research, 2013, 19 (11), 2941-2951.
Tjin Tham Sjin R: In Vitro and In Vivo Characterization of Irreversible Mutant-Selective EGFR Inhibitors That Are Wild-Type Sparing, Molecular Cancer Therapeutics, Jun. 2014, 13 (6), 1468-1479.
Walter et al.: Discovery of a Mutant-Selective Covalent Inhibitor of EGFR that Overcomes T790M-Mediated Resistance in NSCLC, Cancer Discovery, 2013, 3 (12), 1404-1415.

* cited by examiner

A = 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride B = N-[3-[[2-[4-(4-acetylpiperazin-1-yl)-2-methoxy-anilino]-5-(trifluoromethyl)-pyrimidin-4-yl]amino]phenyl]prop-2-enamide A = 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride B = N-[3-[[2-[4-(4-acetylpiperazin-1-yl)-2-methoxy-anilino]-5-(trifluoromethyl)-pyrimidin-4-yl]amino]phenyl]prop-2-enamide

COMBINATION OF A 6-OXO-1,6-DIHYDRO-PYRIDAZINE DERIVATIVE HAVING ANTI-CANCER ACTIVITY WITH AN EGFR INHIBITOR

FIELD OF THE INVENTION

This invention relates to a pharmaceutical composition for cancer disease, which comprises a compound having anti-cancer activity, namely 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof in combination with N-[3-[[2-[4-(4-acetylpiperazin-1-yl)-2-methoxy-anilino]-5-(trifluoromethyl)pyrimidin-4-yl]amino]phenyl]prop-2-enamide.

BACKGROUND OF THE INVENTION

The invention had the object of finding novel pharmaceutical compositions having valuable properties, in particular those which can be used for the preparation of medicaments.

Moreover, aim of this invention are new compositions for the prevention and treatment of neoplastic malignancies including, but without being limited to, solid tumor cancers, cancers of the lymphatic or blood system.

It has been found that the pharmaceutical compositions according to the invention and pharmaceutically acceptable salts and/or solvates thereof have very valuable pharmacological properties while being well tolerated.

Most selective target therapies are when applied as single agents only effective in highly addicted subpopulation of patients. By combining selective target therapies with other targeted agents the anti tumor effect can be enhanced by interfering with cross-talking pathways, blocking different tumor-specific pathways in parallel, or inhibiting the same tumor-specific pathway at different levels to prevent or reduce the risk of progression.

PRIOR ART 3-(1-{3-[5-(1-Methyl-piperidin-4-ylmethoxy)-pyrimidin-2-yl]-benzyl}-6-oxo-1,6-dihydro-pyridazin-3-yl)-benzonitrile has been described in WO 2009/006959 A1.

3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate has been described in WO 2009/007074 A1.

N-[3-[[2-[4-(4-acetylpiperazin-1-yl)-2-methoxy-anilino]-5-(trifluoromethyl)-pyrimidin-4-yl]amino]phenyl]prop-2-enamide

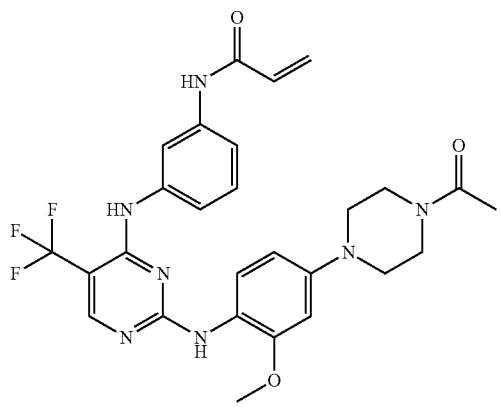 [SMILES: C=CC(=O)Nc1cccc(Nc2nc(Nc3ccc(N4CCN(C(C)=O)CC4)cc3OC)ncc2C(F)(F)F)c1]

is an EGFR inhibitor and has been described in WO 2012/061299.

The compound is useful in the treatment of hyperproliferative diseases, such as cancer.

SUMMARY OF THE INVENTION

Figure 1:
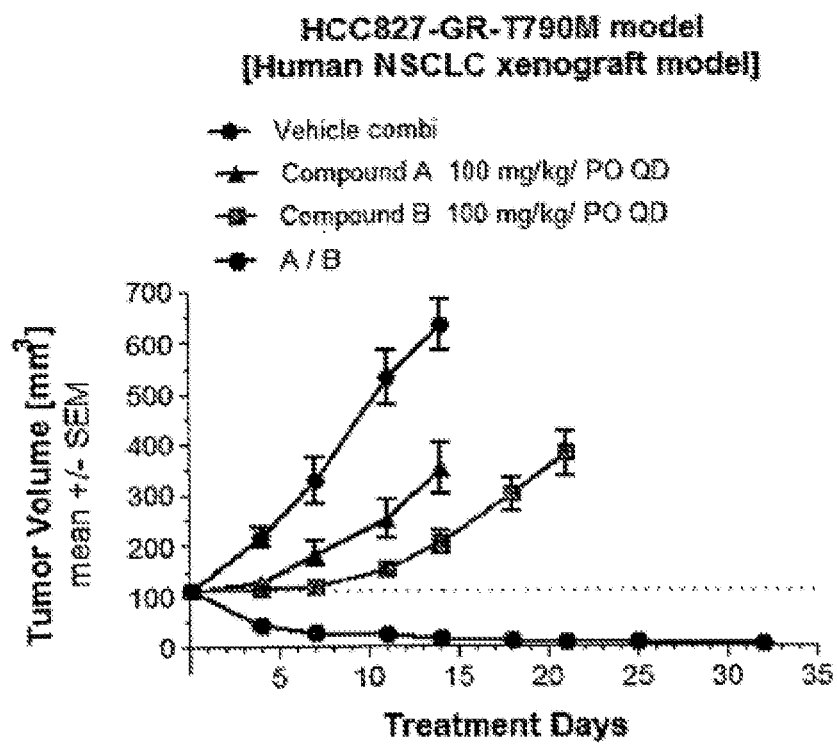
FIG. 1 shows the results of an example concerning the combination of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate and N-[3-[[2-[4-(4-acetylpiperazin-1-yl)-2-methoxy-anilino]-5-(trifluoromethyl)-pyrimidin-4-yl]amino]phenyl]prop-2-enamide in the human NSCLC HCC827-GR-T790M xenograft model.

The invention relates to a pharmaceutical composition of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to a pharmaceutical composition of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to a pharmaceutical composition of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof in combination with N-[3-[[2-[4-(4-acetylpiperazin-1-yl)-2-methoxy-anilino]-5-(trifluoromethyl)pyrimidin-4-yl]amino]phenyl]prop-2-enamide for the use for the treatment of diseases selected from the group cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, the invention relates to a pharmaceutical composition of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate in combination with N-[3-[[2-[4-(4-acetylpiperazin-1-yl)-2-methoxy-anilino]-5-(trifluoromethyl)pyrimidin-4-yl]amino]phenyl]prop-2-enamide for the use for the treatment of cancer, selected from the group small cell lung cancer (SCLC), non-small cell lung cancer (NSCLC), squamous cell cancer of the head and neck (SCCHN).

Moreover, the invention relates to 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof for the use for the treatment of cancer, wherein the medicament is to be used in combination with N-[3-[[2-[4-(4-acetylpiperazin-1-yl)-2-methoxy-anilino]-5-(trifluoromethyl)-pyrimidin-4-yl]amino]phenyl]prop-2-enamide.

Moreover, the invention relates to the use of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof for the manufacture of a medicament for the treatment of cancer, wherein the medicament is to be used in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to the use of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate for the manufacture of a medicament for the treatment of cancer, wherein the medicament is to be used in combination with N-[3-[[2-[4-(4-acetylpiperazin-1-yl)-2-methoxy-anilino]-5-(trifluoromethyl)-pyrimidin-4-yl]amino]phenyl]prop-2-enamide.

Moreover, the invention relates to the use of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate for the manufacture of a medicament for the treatment of cancer, selected from the group colorectal, lung, breast, kidney, and glioblastomas, wherein the medicament is to be used in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to the use of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate for the manufacture of a medicament for the treatment of lung cancer, wherein the medicament is to be used in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to the use of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate for the manufacture of a medicament for the treatment of cancer, selected from the group small cell lung cancer (SCLC), non-small cell lung cancer (NSCLC), squamous cell cancer of the head and neck (SCCHN), wherein the medicament is to be used in combination with N-[3-[[2-[4-(4-acetylpiperazin-1-yl)-2-methoxy-anilino]-5-(trifluoromethyl)pyrimidin-4-yl]amino]phenyl]prop-2-enamide.

Moreover, the invention relates to the use as described above, wherein 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof or 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate is administered to a patient in an amount of 250 mg to 12500 mg per week, preferably in an amount of 800 mg to 8000 mg per week, particularly preferably in an amount of 500 mg to 2000 mg per week.

According to the present invention therapeutically active compositions may also be provided by means of a pharmaceutical kit comprising a package comprising 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof, and N-[3-[[2-[4-(4-acetylpiperazin-1-yl)-2-methoxy-anilino]-5-(trifluoromethyl)pyrimidin-4-yl]amino]phenyl]prop-2-enamide, in single packages or in separate containers.

The therapy with these combinations may include optionally further treatment with radiation. The invention relates furthermore to a new therapy form comprising the start of the administration of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof prior to radiotherapy.

In this new therapy form comprising the start of the administration of 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof prior to radiotherapy, it is a preferred feature that the 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof is administered prior and/or during the administration of N-[3-[[2-[4-(4-acetylpiperazin-1-yl)-2-methoxy-anilino]-5-(trifluoromethyl)-pyrimidin-4-yl]amino]phenyl]prop-2-enamide, preferably at least during a significant part of the treatment regimen. In this context, according to the present invention, radiation, or, radiotherapy preferably has to be understood as a cancer co-therapeutic agent.

The invention also relates to the optically active forms (stereoisomers), the enantiomers, the racemates, the diastereomers and the hydrates and solvates of these compounds.

The invention also relates to the solvates of the salts of the compounds such as the mono- or dihydrate of the hydrochloride.

The term solvates of the compounds is taken to mean adductions of inert solvent molecules onto the compounds which form owing to their mutual attractive force. Solvates are such as mono- or dihydrates or alcoholates.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the invention are for the most part prepared by conventional methods. If the compound of the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the invention are likewise included. In the case of certain compounds of the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzene-sulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound and/or pharmaceutically acceptable salts, solvates, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethyl-cellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds and salts, solvates, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds and the salts, solvates, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt, solvate, tautomer and stereoisomer thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The anti-cancer treatment defined herein may be applied as a sole therapy or may involve, in addition to the composition of the invention, conventional surgery or radiotherapy.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as cancer, The term "therapeutically effective" or "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

Preferably, the compounds are administered once a week, preferably intravenously as infusion. Preferably the initial dose is 100 to 1000 mg per $m^2$ body surface, particurlarly preferably between 200 and 600 mg per $m^2$ body surface.

Subsequent doses are 50 to 600 mg per m$^2$ body surface, particurlarly preferably between 100 and 400 mg per m$^2$ body surface.

Particularly preferably N-[3-[[2-[4-(4-acetylpiperazin-1-yl)-2-methoxy-anilino]-5-(trifluoromethyl)pyrimidin -4-yl] amino]phenyl]prop-2-enamide is administered orally in a tablet twice a day and 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate is administered orally in a tablet once a day. More preferably, the two compounds are administered at the same time orally.

Preferably, 3 N-[3-[[2-[4-(4-acetylpiperazin-1-yl)-2-methoxy-anilino]-5-(trifluoromethyl)pyrimidin-4-yl]amino] phenyl]prop-2-enamide is administered to a patient once or twice a day in an amount of 300 to 900 mg per administration, more preferably in an amount of 400 to 800 mg per administration.

Use

The present compounds are suitable as pharmaceutical active ingredients for mammals, especially for humans, in the treatment of immune modulatory and stress response kinase-induced diseases. These diseases include neoplastic malignancies including, but without being limited to, solid tumor cancers, cancers of the lymphatic or blood system, the proliferation of tumour cells, pathological neovascularisation (or angiogenesis) which promotes the growth of solid tumours, neurodegenerative diseases (Alzheimer, demyelinating core disorders multiple sclerosis and the like), immune related disorders like arthritis, psoriasis, lupus, or other autoimmune diseases as well as chronic infections.

The present invention encompasses the use of the compounds and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas, melanomas and breast carcinoma. A further group of preferred forms of cancer include, but is not limited to, cervical cancer, neuroblastoma, testicular cancer, macroglobulinemia and sarcomas.

The present invention specifically relates to compounds and pharmaceutically acceptable salts, solvates, tautomers and stereoisomers thereof, including mixtures thereof in all ratios, for the use for the treatment of neoplastic malignancies (solid tumor cancers, cancers of the lymphatic or blood system and the like), of neurodegenerative diseases, immune related disorders like arthritis, psoriasis, lupus, multiple sclerosis or other autoimmune diseases as well as chronic infections.

Especial preference is given to the use for the treatment of a disease where the disease is a neoplastic malignancies.

The neoplastic malignancies is preferably selected from the group of tumours of the lung, squamous epithelium, the bladder, the stomach, the kidneys, of head and neck, the esophagus, the cervix, the thyroid, the intestine, the liver, the brain, the prostate, the urogenital tract, the lymphatic system, the stomach and/or the larynx.

The neoplastic malignancies is furthermore preferably selected from the group lung adenocarcinoma, small-cell lung carcinomas, pancreatic cancer, glioblastomas, colon carcinoma and breast carcinoma.

Preference is furthermore given to the use for the treatment of a neoplastic malignancies of the blood and immune system, preferably for the treatment of a tumour selected from the group of acute myeloid leukaemia, chronic myeloid leukaemia, acute lymphatic leukaemia and/or chronic lymphatic leukaemia.

Representative cancers that compounds are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, the present invention specifically relates to compounds for the use for the treatment and/or prevention of cancer, where the cancer to be treated is a solid tumour or a tumour of the blood and immune system.

Moreover, the present invention specifically relates to compounds, for the use for the treatment and/or prevention of cancer, where the where the tumour originates from the group of acute myeloid leukaemia, chronic myeloid leukaemia, acute lymphatic leukaemia and/or chronic lymphatic leukaemia.

Moreover, the present invention specifically relates to compounds, for the use for the treatment and/or prevention of cancer, where the solid tumour originates from the group of tumours of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondosarcoma and Ewing sarcoma, germ cells, including embryonal tissue tumours, and/or the lung, from the group of monocytic leukaemia, lung adenocarcinoma, small-cell lung carcinomas, pancreatic cancer, glioblastomas, neurofibroma, angiosarcoma, breast carcinoma and /or maligna melanoma.

The disclosed compounds of can be administered in combination with other known therapeutic agents, including anticancer agents. As used here, the term "anticancer agent" relates to any agent which is administered to a patient with cancer for the purposes of treating the cancer.

Demonstration that by combining 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate with a third generation EGFR inhibitor, N-[3-[[2-[4-(4-acetylpiperazin-1-yl)-2-methoxy-anilino]-5-(trifluoromethyl)pyrimidin-4-yl]amino]phenyl]prop-2-enamide, the efficacy of N-[3-[[2-[4-(4-acetylpiperazin-1-yl)-2-methoxy-anilino]-5-(trifluoromethyl)pyrimidin-4-yl]amino]phenyl] prop-2-enamide can be improved in lung cancer models, regardless of the EGFR T790M status. Evaluation of the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate/N-[3-[[2-[4-(4-acetylpiperazin-1-yl)-2-methoxy-anilino]-5-(trifluoromethyl)pyrimidin-4-yl] amino]phenyl]prop-2-enamide combination in EGFR T790M mutant model further demonstrated not only enhanced activity compared to N-[3-[[2-[4-(4-acetylpiperazin-1-yl)-2-methoxy-anilino]-5-(trifluoromethyl)pyrimidin-4-yl]amino]phenyl]prop-2-enamide but as well compared to 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate. The enhanced efficacy in the combination group was observed without increase in toxicity as indicated by the lack of significant weight loss or death of animals compared to monotherapies.

Combination of 3-(1-{3-[5-(1-Methyl-piperidin-4-ylmethoxy)-pyrimidin-2-yl]-benzyl}-6-oxo-1,6-dihydropyridazin-3-yl)-benzonitrile hydrochloride hydrate and N-[3-[[2-[4-(4-acetylpiperazin-1-yl)-2-methoxy-anilino]-5-(trifluoromethyl)-pyrimidin-4-yl]amino]phenyl]prop-2-enamide in the human NSCLC HCC827-GR-T790M xenograft model:

Background: The human NSCLC HCC827-GR-T790M is a EGFR del 19 mutant and c-Met amplified lung xenograft model which exogenous expression of the EGFR T790M resistant mutation. This model is resistant to EGFR inhibitors erlotinib and afatinib due to the acquired resistance through c-Met amplification and the EGFR T790M mutation.

Method: Female NCr nude mice (7 weeks old) where subcutaneously injected with human HCC827-GR-T790M tumor cells and were divided into treatment groups (10 animals per group) after the tumors were established. Respective groups were administered orally with the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate (100 mg/kg) or N-[3-[[2-[4-(4-acetylpiperazin-1-yl)-2-methoxy-anilino]-5-(trifluoromethyl)pyrimidin-4-yl]amino]phenyl]prop-2-enamide (100 mg/kg) daily in monotherapy or in combination until group tumor volume mean reached 300 mm$^3$ or up to 32 days. Median tumor volume (TV) change in % were calculated at day 14, where the vehicle group was terminated and statistical analysis done with two way-RM ANOVA.

Results: Under 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate and N-[3-[[2-[4-(4-acetylpiperazin-1-yl)-2-methoxy-anilino]-5-(trifluoromethyl)-pyrimidin-4-yl]amino]phenyl]prop-2-enamide monotherapy treatment tumors progressed resulting in a median tumor volume change of 205% (p<0.01) and 81% (p<0.0001), respectively. Combination of both agents statistically significant enhanced anti-tumor activity compared to best single agent N-[3-[[2-[4-(4-acetylpiperazin-1-yl)-2-methoxy-anilino]-5-(trifluoromethyl)pyrimidin-4-yl]amino] phenyl]prop-2-enamide resulting in complete tumor regression (median TV change of −87%, p<0.0001) in all mice. After long term combination treatment up to 32 days, non-palpable tumors were observed in 5 out of 8 mice. (Tumor progression: median TV change >73%; tumor stasis/regression: median TV change <73%; complete tumor regression: non palpable tumors or tumor volume <20 mm$^3$ compared to start tumor volume.) Monotherapies and combination treatment have been tolerated well. Results are shown in FIG. 1.

Combination of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate and N-[3-[[2-[4-(4-acetylpiperazin-1-yl)-2-methoxy-anilino]-5-(trifluoromethyl)-pyrimidin-4-yl]amino]phenyl]prop-2-enamide in a human DFCI081 patient derived NSCLC xenograft (PDX)model:

Background: The human DFCI081 NSCLC xenograft is a EGFR del 19 mutant and c-Met amplified lung tumor and resistant to EGFR inhibitors erlotinib and afatinib due to the activated c-Met pathway.

Method: Female NCr nude mice (7 weeks old) where subcutaneously injected with human DFCI081 tumor cells and were divided into treatment groups (10 animals per group) after the tumors were established. Respective groups were administered orally with the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate (100 mg/kg) or N-[3-[[24-[4-(4-acetylpiperazin-1-yl)-2-methoxy-anilino]-5-(trifluoromethyl)pyrimidin-4-yl]amino]phenyl]prop-2-enamide (100 mg/kg) daily in monotherapy or in combination up to 18 days. Median tumor volume (TV) change in % were calculated and statistical analysis done with two way-RM ANOVA.

Figure 2:
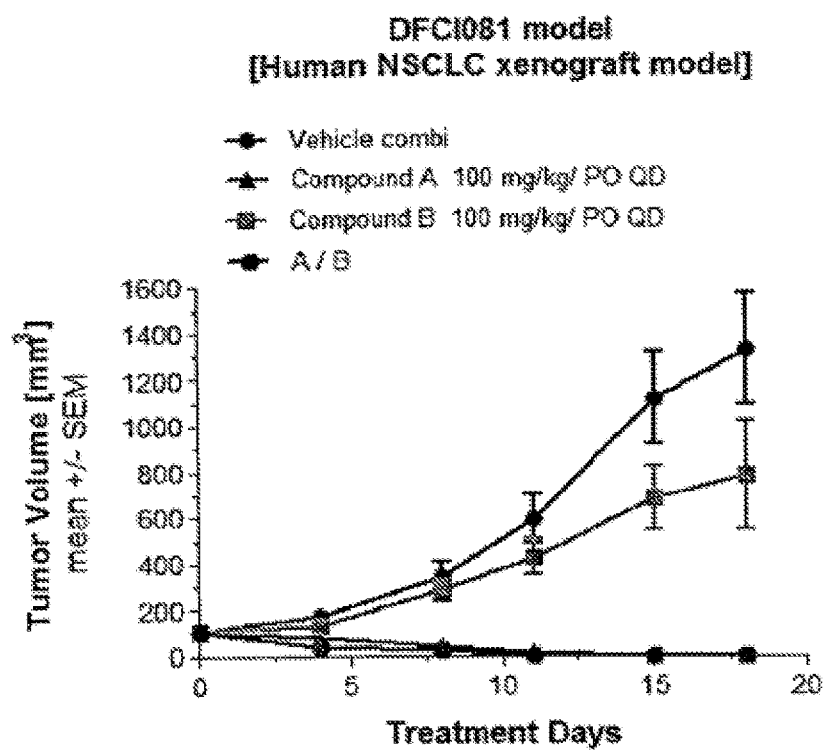
FIG. 2 shows the results of an example concerning the combination of 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate and N-[3-[[2-[4-(4-acetylpiperazin-1-yl)-2-methoxy-anilino]-5-(trifluoromethyl)-pyrimidin-4-yl]amino]phenyl]prop-2-enamide in a human DFCI081 patient derived NSCLC xenograft (PDX)model.

Results: 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate showed strong anti-tumor activity resulting in tumor regression (TV change of −100%, p<0.0001). Complete tumor regression in all mice has been observed at day 15. Under treatment with N-[3-[[2-[4-(4-acetylpiperazin-1-yl)-2-methoxy-anilino]-5-(trifluoromethyl)pyrimidin-4-yl]amino]phenyl]prop-2-enamide, tumor progressed resulting in a median tumor volume change of 700% (ns). Combination of both agents did not statistically significant enhanced anti-tumor activity compared to best single agent 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate but complete tumor response in the combination group has been induced in all mice earlier at day 11. (Tumor progression: median TV change>73%; tumor stasis/regression: median TV change<73%; complete tumor regression: non palpable tumors or tumor volume<20mm$^3$ compared to start tumor volume.) Monotherapies and combination treatment have been tolerated well. Results are shown in FIG. 2.

The invention claimed is:

1. A method for treating non-small cell lung cancer, comprising administering to a subject in need thereof an effective synergistic amount of a pharmaceutical composition comprising 3-(1-{3[5-(1-Methyl-piperidin-4-ylmethoxy)-pyrimidin-2-yl]benzyl}-6-oxo-1,6-dihydro-pyridazin-3-yl)-benzonitrile or a pharmaceutically acceptable salt and/or solvate thereof and N-[3-[[2-[4-(4-acetylpiperazin-1-yl)-2-methoxy-anilino]-5(trifluoromethyl)pyrimidin-4-yl]amino]phenyl]prop-2-enamide.

2. The method according to claim 1, comprising administering to a subject in need thereof an effective amount of a pharmaceutical composition comprising 3-(1-{3-[5-(1-Methyl-piperidin-4-ylmethoxy)-pyrimidin-2-yl ]-benzyl}-6-oxo-1,6-dihydro-pyridazin-3-yl)-benzonitrile hydrochloride hydrate and N-[3-[[2-[4-(4-acetylpiperazin-1-yl)-2-methoxy-anilino]-5-(trifluoromethyl)pyrimidin-4-yl]amino]phenyl]prop-2-enamide.

3. The method according to claim 1, wherein the 3 N-[3-[[2-[4-(4-acetylpiperazin-1-yl)-2-methoxy-anilino]-5-(trifluoromethyl)pyrimidin-4-yl]amino]phenyl]prop-2-enamide is administered once or twice a day in an amount of 300 to 900 mg per administrationin.

4. The method according to claim 1, wherein the 3 N-[3-[[2-[4-(4-acetylpiperazin-1-yl)-2-methoxy-anilino]-5-(trifluoromethyl)pyrimidin-4-yl]amino]phenyl]prop-2-enamide is administered once or twice a day in an amount of 300 to 900 mg per administration and the 3-(1-{3-[5-(1Methyl-piperidin-4-ylmethoxy)-pyrimidin-2-yl]-benzyl}-6-oxo-1,6-dihydro-pyridazin-3-yl)-benzonitrile or a pharmaceutically acceptable salt thereof and/or solvate thereof is administered in an amount of 250 mg to 12500 mg per week.

5. The method according to claim 2, wherein the 3 N-[3-[[2-[4-(4-acetylpiperazin-1-yl)-2-methoxy-anilino]-5-(trifluoromethyl)pyrimidin-4-yl]amino]phenyl]prop-2-enamide is administered once or twice a day in an amount of 300 to 900 mg per administration and the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate is administered in an amount of 250 mg to 12500 mg per week.

6. The method according to claim 1, wherein the 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof in combination with N-[3-[[2-[4-(4-acetylpiperazin-1-yl)-2-methoxy-anilino]-5-(trifluoromethyl)pyrimidin-4-yl]amino]phenyl]prop-2-enamide is administered in a synergistic amount.

7. The method according to claim 1, wherein the 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt and/or solvate thereof is administered in an amount of 250 mg to 12500 mg per week.

8. The method according to claim 2, wherein the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate is administered in an amount of 250 mg to 12500 mg per week.

9. The method according to claim 2, wherein the 3-(1-{3-[5-(1-Methyl-piperidin-4-ylmethoxy)-pyrimidin-2-yl]-benzyl}-6-oxo-1,6-dihydro-pyridazin-3-yl)-benzonitrile hydrochloride hydrate in combination with N-[3-[[2-[4-(4-acetylpiperazin-1-yl)-2-methoxy-anilino]-5-(trifluoromethyl)pyrimidin-4-yl]amino]phenyl]prop-2-enamide is administered in a synergistic amount.

10. The method according to claim 1, wherein the 3-(1-{3-[5-(1-Methyl-piperidin-4-ylmethoxy)-pyrimidin-2-yl]-benzyl}-6-oxo-1,6-dihydro-pyridazin-3-yl)-benzonitrile or a pharmaceutically acceptable salt thereof is administered in an amount of 250 mg to 12500 mg per week.

* * * * *